(12) United States Patent
Houze

(10) Patent No.: US 6,583,165 B2
(45) Date of Patent: Jun. 24, 2003

(54) ARYLSULFONANILIDE UREAS

(75) Inventor: Jonathan B. Houze, San Mateo, CA (US)

(73) Assignee: Tularik Inc., South San Francisco, CA (US)

( * ) Notice: Subject to any disclaimer, the term of this patent is extended or adjusted under 35 U.S.C. 154(b) by 122 days.

(21) Appl. No.: 09/792,669

(22) Filed: Feb. 21, 2001

(65) Prior Publication Data

US 2001/0027211 A1 Oct. 4, 2001

Related U.S. Application Data

(62) Division of application No. 09/399,907, filed on Sep. 21, 1999, now Pat. No. 6,214,880.
(60) Provisional application No. 60/100,888, filed on Sep. 23, 1998.

(51) Int. Cl.$^7$ .................. A61K 31/4196; A61K 31/415; C07D 249/14; C07D 231/42
(52) U.S. Cl. .................... 514/383; 514/237.5; 514/363; 514/371; 514/381; 514/407; 514/471; 544/159; 548/140; 548/196; 548/251; 548/365.4; 548/371.7; 549/493
(58) Field of Search .............................. 548/371.7, 196, 548/251, 140, 365.4; 549/493; 544/159; 514/407, 471, 363, 371, 381, 383, 237.5

(56) References Cited

U.S. PATENT DOCUMENTS

| | | |
|---|---|---|
| 1,955,207 A | 4/1934 | Stotter et al. |
| 2,358,365 A | 9/1944 | Tullar |
| 2,402,623 A | 6/1946 | Hester et al. |
| 3,034,955 A | 5/1962 | Frick et al. |
| 4,881,969 A | 11/1989 | Saupe et al. |
| 4,883,914 A | 11/1989 | Alvarado et al. |
| 4,900,867 A | 2/1990 | Wilkes et al. |
| 5,143,937 A | 9/1992 | Lang et al. |
| 5,189,211 A | 2/1993 | Sato et al. |
| 5,250,549 A | 10/1993 | Yoshino et al. |
| 5,385,931 A | 1/1995 | Bigg et al. |
| 5,387,709 A | 2/1995 | Lardy et al. ................. 514/311 |
| 5,780,483 A | 7/1998 | Widdowson et al. |

FOREIGN PATENT DOCUMENTS

| | | |
|---|---|---|
| DE | 622 494 C | 11/1935 |
| DE | 36 23 184 A | 1/1988 |
| EP | 0 391 799 A | 10/1990 |
| EP | 0 469 901 A | 2/1992 |
| EP | 0 472 449 A | 2/1992 |
| EP | 0472053 A | 2/1999 |
| FR | 2456731 A | 12/1980 |
| GB | 859 345 A | 1/1961 |
| GB | 938 890 A | 10/1963 |
| GB | 1 189 720 A | 4/1970 |
| GB | 1 242 057 A | 8/1971 |
| GB | 1 306 564 A | 2/1973 |
| WO | WO 97/30677 A2 | 8/1997 |
| WO | WO 98/05315 | 2/1998 |

OTHER PUBLICATIONS

Fielding et al, "Synthesis and Reactions of 4–sulpho–2,3,5, 6–Tetrafluorobenzoic Acid"; *Journal of Fluorine Chemistry*, vol. 59, No. 1, pp. 15–31 (1992).

Raibekas et al. "Affinity Probing of Flavin Binding Sites. 2. Identification of Reactive cysteine in the Flavin Domain of *Escherichia coli* DNA Photolyase"; *Biochemistry*, vol. 33, No. 42, pp. 12656–12664 (1994).

Shealy et al. "2–Haleothylating Agents for Cancer Chemotherapy. 2–Haloethyl Sulfonates"; *Journal of Medicinal Chemistry*, vol. 26, pp. 1168–1173 (Aug. 1983).

Olander et al., "A Study of the binding of two sulfonamides to Carbonic Anhydrase"; *Journal of American Chemical Society*, vol. 95, No. 5, pp. 1616–1621 (Mar. 7, 1973).

Hawkinson, et al; "Studies of the Solvolysis of 2–Adamantyl Pentafluorobenzenesulfonate: A $Y_{PFBS}$ Scale"; *The Journal of Organic Chemistry*, Aug. 1988, vol. 53, No. 16, pp. 3857–3860.

Chemical Abstracts, vol. 50, No. 1, Jan. 10, 1956, Columbus, Ohio, US; abstract No. 217g, V.O. Lukashevich: "Sulphonation of halogen–substituted benzene derivatives. formation of anhydrides of corresponding sulphonic acids" col. 217; XP002083056 see abstract & Doklady Akad. Nauk S.S.S.R., vol. 99, 1954, pp. 995–998.

Chemical Abstracts, vol. 74, No. 14, Apr. 5, 1971, Columbus, Ohio, US; abstract No. 65535a, D. Simov, Et al.: "Preparation of azo dyes containing amobile chlorine atom in the benzene ring" p. 81: XP002083055 see abstract & IZV. OTD. KHIM. NAUKI, BULG. AKAD. NAUK, vol. 3, No. 1, 1970, pp. 69–82.

I.C. Poppoff, et al.: "Antimalarial agents. 8. Ring–substituted bis–(4–aminophenyl) sulphones and their precursors" *Journal of Medicinal Chemistry*, vol. 14, No. 12, Dec. 1971, pp. 1166–1169, XP002083052 Washington, DC, US see comounds V, VIII,X, XI, XIII, XVII, XIX, XXVIII, XXXII, XXXVI–XXXVIII, XLI, XLII<XLIV<XLV.

G.E. Chivers, et al.: "Studies in the chemistry of polyhalogenobenzene compounds. The synthesis and reactivity of 2,3,5,6– and 2,3,4,5–tetrachlorobenzenesulphony chlorides and related compounds"; *Australian Journal of Chemistry*, vol. 29, No. 7, Jul. 1976, pp. 1572–1582, XP002083174, Melbourne, AU.

(List continued on next page.)

*Primary Examiner*—Laura L. Stockton
(74) *Attorney, Agent, or Firm*—Townsend and Townsend and Crew LLP

(57) ABSTRACT

The invention provides compounds, compositions and methods relating to novel arylsulfonanilide derivatives and their use as pharmacologically active agents. The compositions find particular use as pharmacological agents in the treatment of disease states, particularly cancer, psoriasis, vascular restenosis, infections, atherosclerosis and hypercholesterolemia, or as lead compounds for the development of such agents.

33 Claims, No Drawings

OTHER PUBLICATIONS

P.G. DeBenedetti, et al.; "Quantitative structure–activity analysis in dihydropteroate synghase inhibition by sulphones. Comparison with sulphanilamides" *Journal of Medicinal Chemistry*, vol. 30, No. 3, Mar. 1987, pp. 459–464. XP002083053 Washington, DC, US.

V.N. Babushkin, et al.: "Influence of substituents on the frequency of stretching vibrations of sulphur–containing bridging groups in diphenyl systems" *Journal of General Chemistry of the USSR*, vol. 58, No. 7, pt. 2, Jul. 1988, pp. 1457–1460. XP002083054 New York, US.

Yoshimoto and Hansch, "Correlation Analysis of Baker's Studies on Enzyme Inhibition. 2. Chymotrypsin, Thymidine Phosphorylase, Uridine Phosphorylase, Thymidylate Synthetase, Cytosine Nucleoside Deaminase, Dihydrofolate Reductase, malate Dehydrogenase, Glutamate Dehydrogenase, Lactate Dehydrogenase, and Glyceraldehyde–phosphate Dehydrogenase."; *Journal of Medicinal Chemistry* (1976) vol. 19, No. 1 pp. 71–98.

Bai, et al.; "Identification of the cystein Residue of β–Tubulin Alkylated by the Antimitotic Agent 2,4–Dichlorobenzyl Thiocyanate, Facilitated by Separationof the Protein subunits of Tubulin by Hydrophobic column chromotography"; *Biochemistry*, 1989, vol. 28, pp. 5606–5612.

ARYLSULFONANILIDE UREAS

CROSS-REFERENCES TO RELATED APPLICATIONS

This application is a divisional of and claims the benefit of U.S. Ser. No. 09/399,907, filed Sep. 21, 1999; now U.S. Pat. No. 6,214,880, and U.S. Ser. No. 60/100,888, filed Sep. 23, 1998, the disclosures of each being incorporated by reference.

FIELD OF THE INVENTION

The present invention relates to arylsulfonanilide ureas and their use as pharmacologically active agents capable of lowering plasma cholesterol levels and inhibiting abnormal cell proliferation.

BACKGROUND OF THE INVENTION

A number of arylsulfonamides have recently been described for the treatment of disorders and conditions arising from abnormal cell proliferation and from elevated plasma cholesterol levels. See, for example, PCT publications WO 97/30677 and WO 98/05315.

Most prevalent among diseases stemming from abnormal cell proliferation is cancer, a generic name for a wide range of cellular malignancies characterized by unregulated growth, lack of differentiation, and the ability to invade local tissues and metastasize. These neoplastic malignancies affect, with various degrees of prevalence, every tissue and organ in the body. A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disruptors (e.g., vincristine, vinblastine, paclitaxel), DNA intercalators (e.g., doxorubicin, daunomycin, cisplatin), and hormone therapy (e.g., tamoxifen, flutamide). The ideal antineoplastic drug would kill cancer cells selectively, with a wide therapeutic index relative to its toxicity towards non-malignant cells. It would also retain its efficacy against malignant cells, even after prolonged exposure to the drug. Unfortunately, none of the current chemotherapies possess an ideal profile. Most possess very narrow therapeutic indexes and, in practically every instance, cancerous cells exposed to slightly sublethal concentrations of a chemotherapeutic agent will develop resistance to such an agent, and quite often cross-resistance to several other antineoplastic agents.

Psoriasis, a common chronic skin disease characterized by the presence of dry scales and plaques, is generally thought to be the result of abnormal cell proliferation. The disease results from hyperproliferation of the epidermis and incomplete differentiation of keratinocytes. Psoriasis often involves the scalp, elbows, knees, back, buttocks, nails, eyebrows, and genital regions, and may range in severity from mild to extremely debilitating, resulting in psoriatic arthritis, pustular psoriasis, and exfoliative psoriatic dermatitis. No therapeutic cure exists for psoriasis. Milder cases are often treated with topical corticosteroids, but more severe cases may be treated with antiproliferative agents, such as the antimetabolite methotrexate, the DNA synthesis inhibitor hydroxyurea, and the microtubule disrupter colchicine.

Other diseases associated with an abnormally high level of cellular proliferation include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection, where endothelial cells are involved, infectious diseases such as HIV infection and malaria, where certain immune cells and/or other infected cells are involved, and the like. Infectious and parasitic agents per se (e.g. bacteria, trypanosomes, fungi, etc) are also subject to selective proliferative control using the subject compositions and compounds.

Psoriasis, a common chronic skin disease characterized by the presence of dry scales and plaques, is generally thought to be the result of abnormal cell proliferation. The disease results from hyperproliferation of the epidermis and incomplete differentiation of keratinocytes. Psoriasis often involves the scalp, elbows, knees, back, buttocks, nails, eyebrows, and genital regions, and may range in severity from mild to extremely debilitating, resulting in psoriatic arthritis, pustular psoriasis, and exfoliative psoriatic dermatitis. No therapeutic cure exists for psoriasis. Milder cases are often treated with topical corticosteroids, but more severe cases may be treated with antiproliferative agents, such as the antimetabolite methotrexate, the DNA synthesis inhibitor hydroxyurea, and the microtubule disrupter colchicine.

Other diseases associated with an abnormally high level of cellular proliferation include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection, where endothelial cells are involved, infectious diseases such as HIV infection and malaria, where certain immune cells and/or other infected cells are involved, and the like. Infectious and parasitic agents per se (e.g. bacteria, trypanosomes, fungi, etc) are also subject to selective proliferative control using the subject compositions and compounds.

Psoriasis, a common chronic skin disease characterized by the presence of dry scales and plaques, is generally thought to be the result of abnormal cell proliferation. The disease results from hyperproliferation of the epidermis and incomplete differentiation of keratinocytes. Psoriasis often involves the scalp, elbows, knees, back, buttocks, nails, eyebrows, and genital regions, and may range in severity from mild to extremely debilitating, resulting in psoriatic arthritis, pustular psoriasis, and exfoliative psoriatic dermatitis. No therapeutic cure exists for psoriasis. Milder cases are often treated with topical corticosteroids, but more severe cases may be treated with antiproliferative agents, such as the antimetabolite methotrexate, the DNA synthesis inhibitor hydroxyurea, and the microtubule disrupter colchicine.

Other diseases associated with an abnormally high level of cellular proliferation include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection, where endothelial cells are involved, infectious diseases such as HIV infection and malaria, where certain immune cells and/or other infected cells are involved, and the like. Infectious and parasitic agents per se (e.g. bacteria, trypanosomes, fungi, etc) are also subject to selective proliferative control using the subject compositions and compounds.

Accordingly, it is one object of the present invention to provide compounds which directly or indirectly are toxic to actively dividing cells and are useful in the treatment of cancer, viral and bacterial infections, vascular restenosis, inflammatory diseases, autoimmune diseases, and psoriasis.

A further object of the present invention is to provide therapeutic compositions for treating the conditions described herein.

Still further objects are to provide methods for killing actively proliferating cells, such as cancerous, bacterial, or epithelial cells, and treating all types of cancers, infections, inflammatory, and generally proliferative conditions. A further object is to provide methods for treating other medical conditions characterized by the presence of rapidly proliferating cells, such as psoriasis and other skin disorders.

Additional objects, features and advantages will become apparent to those skilled in the art from the following description and claims.

SUMMARY OF THE INVENTION

The invention provides novel arylsulfonanilide compounds, as well as methods and compositions relating to novel arylsulfonanilide ureas and their use as pharmacologically active agents. The compounds and compositions find use as pharmacological agents in the treatment of disease states, particularly hypercholesterolemia, atherosclerosis, cancer, bacterial infections, and psoriasis, or as lead compounds for the development of such agents. The compounds of the invention have the formula:

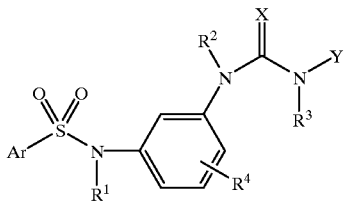

I or a pharmaceutically acceptable salt thereof.

In the formula above, X represents an oxygen atom, a sulfur atom or NH, preferably oxygen.

The letter Y represents hydrogen, a heterocyclic ring, $(C_1-C_8)$alkyl, $(C_1-C_8)$heteroalkyl, aryl, aryl$(C_1-C_4)$alkyl, aryl$(C_1-C_4)$heteroalkyl, heteroaryl$(C_1-C_4)$alkyl, heteroaryl $(C_1-C_4)$heteroalkyl, or is optionally linked together with $R^3$ to form a 5-, 6- or 7-membered heterocyclic ring which can be aromatic or non-aromatic.

The symbols $R^1$, $R^2$ and $R^3$ each independently represent hydrogen, $(C_1-C_6)$alkyl or $(C_1-C_6)$heteroalkyl. Additionally, as noted above, in some embodiments $R^3$ is combined with Y and the adjacent nitrogen atom to form a heterocyclic ring. The symbol $R^4$ represents hydrogen, halogen, $(C_1-C_8)$alkyl, $(C_1-C_8)$heteroalkyl, —$OR^{11}$, —$SR^{11}$ and —$NR^{11}R^{12}$, wherein $R^{11}$ and $R^{12}$ are each independently hydrogen, $(C_1-C_8)$alkyl or $(C_1-C_8)$ heteroalkyl.

The symbol Ar represents a substituted aryl group selected from

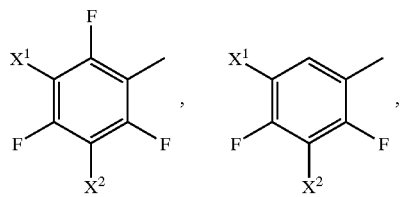

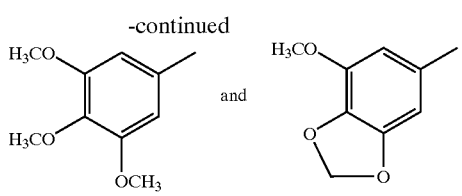

in which $X^1$ and $X^2$ are each independently F, Cl or Br.

The methods of the present invention use pharmaceutical compositions containing compounds of the foregoing description of the general Formula I for the treatment of pathology such as cancer, bacterial infections, psoriasis, hypercholesterolemia, atherosclerosis, pancreatitis, and hyperlipoproteinemia. Briefly, the inventions involve administering to a patient an effective formulation of one or more of the subject compositions.

BRIEF DESCRIPTION OF THE DRAWINGS

Not applicable

DETAILED DESCRIPTION OF THE INVENTION

Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multi-radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "alkoxy," employed alone or in combination with other terms means, unless otherwise stated, an alkyl group, as defined above, connected to the remainder of the molecule via an oxygen atom, such as, for example, methoxy, ethoxy, 1-propoxy, 2-propoxy and the higher homologs and isomers.

The term "thioalkoxy," employed alone or in combination with other terms means, unless otherwise stated, an alkyl group, as defined above, connected to the remainder of the molecule via a sulfur atom, such as, for example, thiomethoxy (methylthio), thioethoxy (ethylthio), 1-thiopropoxy, 2-thiopropoxy and the higher homologs and isomers.

The term "heteroalkyl," by itself or in combination with another term, means, unless otherwise stated, a stable straight or branched chain, or cyclic hydrocarbon radical, or combinations thereof, which may be fully saturated, mono- or polyunsaturated and can include di- and multi-radicals, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, as well as all other linking groups described herein, no specific orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a carbon atom or a heteroatom. Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

The terms "arylalkyl" and "arylheteroalkyl" are meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 1-naphthyloxy-3-propyl, and the like). The arylalkyl and arylheteroalkyl groups will typically contain from 1 to 3 aryl moieties attached to the alkyl or heteroalkyl portion by a covalent bond or by fusing the ring to, for example, a cycloalkyl or heterocycloalkyl group. For arylheteroalkyl groups, a heteroatom can occupy the position at which the group is attached to the remainder of the molecule. For example, the term "arylheteroalkyl" is meant to include benzyloxy, 2-phenylethoxy, phenethylarnine, and the like.

As used herein, the term "heterocycle" refers to any ring having at least one heteroatom ring member. The term is meant to be inclusive of both heterocycloalkyl groups, heteroaryl groups and other rings having one or more heteroatoms and optionally one or more unsaturated bonds (typically, a double bond). In addition to the examples provided above for heterocycloalkyl and heteroaryl groups, the term "heterocycle" includes 1,2,4-triazolyl, 1,3,4-thiadiazolyl, pyrazolyl, 1,2,3,4-tetrazolyl and 1,2,3-triazolyl. As with heteroaryl groups, heterocyclic groups can be attached to the remainder of the molecule through either a carbon atom or a heteroatom ring member.

Each of the above terms (e.g., "alkyl," "heteroalkyl," "aryl" and "heterocycle") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', —halogen, —SiR'R"R'", —OC(O)R', —$CO_2$R', —CONR'R", —OC(O)NR'R", —NR"C(O)R', —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2N+1), where N is the total number of carbon atoms in such radical. R', R" and R'" each independently refer to hydrogen, unsubstituted($C_1$–$C_8$)alkyl and heteroalkyl, unsubstituted aryl, aryl substituted with 1–3 halogens, unsubstituted alkyl, alkoxy or thioalkoxy groups, or aryl—($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl.

Similarly, substituents for the aryl groups are varied and are selected from: —halogen, —OR', —OC(O)R', —NR'R", —SR', —R', —CN, —$NO_2$, —$CO_2$R', —CONR'R", —OC(O)NR'R", —NR"C(O)R', —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R' and R" are independently selected from hydrogen, ($C_1$–$C_8$)alkyl and heteroalkyl, unsubstituted aryl, (unsubstituted aryl)—($C_1$–$C_4$)alkyl, and (unsubstituted aryl)oxy-($C_1$–$C_4$)alkyl.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of formula I. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

The compounds described herein are related to compounds provided in PCT publications WO 97/30677 and WO 98/05315, and to compounds provided in co-pending application Ser. No. 08/917,025 (filed Aug. 22, 1997) and application Ser. No. 60/090,681 (Atty Docket No. T98-014, filed Jun. 25, 1998). More particularly, compounds are now described in which a urea or substituted urea, thiourea or substituted thiourea, or guanidine or substituted guanidine moiety is attached to an arylsulfonamidobenzene.

Embodiments of the Invention

The present invention provides novel arylsulfonanilide derivatives having the formula:

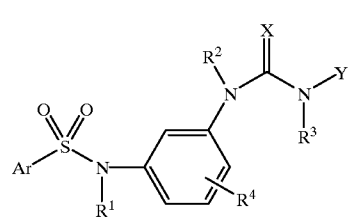

I or a pharmaceutically acceptable salt thereof.

In the above formula, the letter X represents O, S, or NH, preferably O. The letter Y represents hydrogen, a heterocyclic ring, (C$_1$–C$_8$)alkyl, (C$_1$–C$_8$)heteroalkyl, aryl, aryl (C$_1$–C$_4$)alkyl, aryl(C$_1$–C$_4$)heteroalkyl, heteroaryl(C$_1$–C$_4$) alkyl or heteroaryl(C$_1$–C$_4$)heteroalkyl. Optionally, Y is linked together with R$^3$ to form a 5-, 6- or 7-membered heterocyclic ring.

In one group of preferred embodiments, Y is a substituted or unsubstituted (C$_1$–C$_8$)alkyl, or a substituted or unsubstituted (C$_1$–C$_8$)heteroalkyl. Preferably, Y is selected from 2-methoxyethyl, 2-hydroxyethyl, 2,3-dihydroxypropyl and 3-hydroxypropyl.

In another group of preferred embodiments, Y is a substituted or unsubstituted heterocycle (e.g., 2-thiadiazolyl, 5-tetrazolyl, 2-thiazolyl, and the like) or a substituted or unsubstituted aryl group.

In yet another group of preferred embodiments, Y is a substituted or unsubstituted aryl($C_1$–$C_4$)alkyl, aryl($C_1$–$C_4$) heteroalkyl, heteroaryl($C_1$–$C_4$)alkyl or heteroaryl($C_1$–$C_4$) heteroalkyl group. Example of these groups include benzyl, phenethyl, furfurylmethyl, furfurylethyl, thienylmethyl, thienylethyl and the like. A particularly preferred member of this group of embodiments is 2-furfurylmethyl.

In still another group of preferred embodiments, Y is combined with $R^3$ and the nitrogen atom to which each is attached to form a heterocyclic ring, preferably monocyclic and having five or six ring vertices. The heterocyclic ring formed by Y, N and $R^3$ can be substituted or unsubstituted. Examples of such rings include 3-aminopyrazole, 3-amino-1,2,4-triazole, and 4-morpholine. Particularly preferred are the 3-amino-1,2,4-triazole ring and the 3-aminopyrazole ring.

Returning to the general formula above, the symbols $R^1$ and $R^2$ are each independently hydrogen, ($C_1$–$C_6$)alkyl or ($C_1$–$C_6$)heteroalkyl. Preferably, $R^1$ and $R^2$ are each independently hydrogen or ($C_1$–$C_4$)alkyl. More preferably, $R^1$ and $R^2$ are both hydrogen.

The symbol $R^3$ represents hydrogen, ($C_1$–$C_6$)alkyl or ($C_1$–$C_6$)heteroalkyl, or can be combined with Y as described above to form a heterocyclic ring. Preferably, $R^3$ is hydrogen or is combined with Y to form a five- or six-membered heterocyclic ring.

The symbol $R^4$ represents hydrogen, halogen, ($C_1$–$C_8$) alkyl, ($C_1$–$C_8$)heteroalkyl, —$OR^{11}$, —$SR^{11}$ or —$NR^{11}R^{12}$, wherein $R^{11}$ and $R^{12}$ are each independently hydrogen, ($C_1$–$C_8$)alkyl or ($C_1$–$C_8$)heteroalkyl. In preferred embodiments, $R^4$ is attached to the position para to the sulfonamide group (and ortho to the urea). Particularly preferred are those embodiments in which $R^4$ is hydrogen, ($C_1$–$C_3$)alkyl or ($C_1$–$C_3$)alkoxy, more preferably ($C_1$–$C_3$) alkoxy.

The symbol Ar represents a substituted aryl group selected from

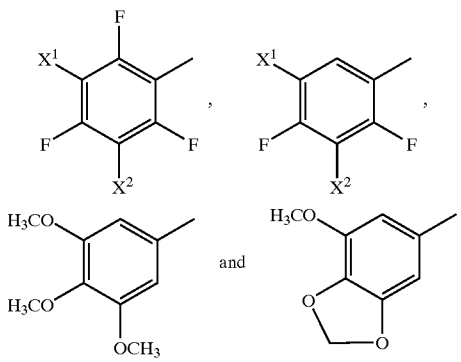

in which $X^1$ and $X^2$ are each independently F, Cl or Br. In one group of preferred embodiments, Ar is pentafluorophenyl. In another group of preferred embodiments, Ar is 2,3,4,5-tetrafluorophenyl. In yet another group of preferred embodiments, Ar is 3,4,5-trimethoxyphenyl. In still another group of preferred embodiments, Ar is 3-methoxy-4,5-methylenedioxyphenyl.

Certain combinations of the above preferred embodiments are particularly preferred. In a first group of preferred embodiments, the compounds have the formula:

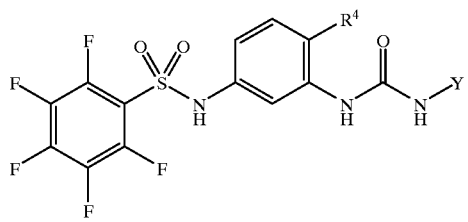

In this group of embodiments, $R^4$ is preferably hydrogen, ($C_1$–$C_3$)alkyl, ($C_1$–$C_3$)alkoxy or ($C_1$–$C_3$)thioalkoxy, more preferably, methyl, methoxy, ethoxy or thiomethoxy. Y is preferably hydrogen, a heterocyclic ring, ($C_1$–$C_8$)alkyl, ($C_1$–$C_8$)heteroalkyl, aryl or aryl($C_1$–$C_4$)alkyl, most preferably hydrogen.

In another group of preferred embodiments, the compounds have the formula:

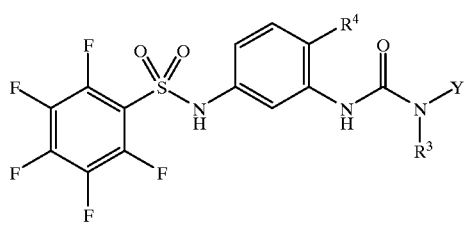

In this group of embodiments, $R^4$ is the same as described for formula Ia. $R^3$ and Y are preferably combined to form a substituted or unsubstituted heterocyclic ring. Preferred groups for the ring defined by $R^3$, Y and the nitrogen to which each is attached include 3-amino-pyrazole, 3-amino-1,2,4-triazole, and 4-morpholine.

Synthesis

Compounds of the present invention can be prepared using certain intermediates and methods described in WO 97/30677 and WO 98/05315. In one group of embodiments, arylsulfonamidoanilines can be prepared as described, and the anilino amino group can then be acylated with an appropriate isocyanate derivative using conventional methods. For example, 2-methoxy-5-pentafluorophenylsulfonamidoaniline can be treated with an isocyanate (e.g., ethyl isocyanatoacetate, potassium isocyanate, and the like) to form compounds of the present invention (see, Examples 5 and 6). In a similar manner, additional compounds can be formed beginning with the appropriate aniline derivative. Using thioisocyanates in place of isocyanates allows for the synthesis of the corresponding thioureas. A general scheme for the preparation of ureas and thioureas using isocyanates and thioisocyanates, respectively, is provided in Scheme 1, which further illustrates the preparation of guanidine derivatives from a thiourea.

SCHEME 1

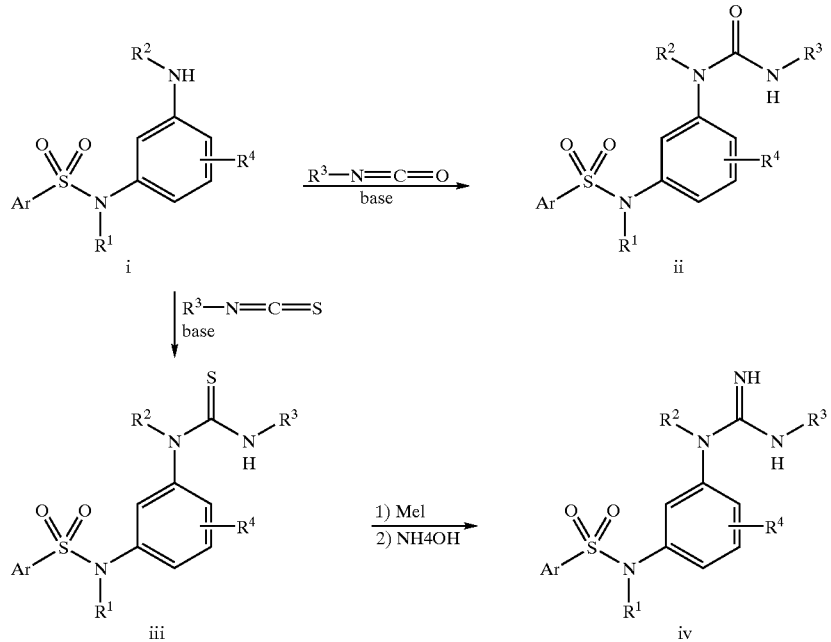

As shown in Scheme 1, an arylsulfonamidoaniline i can be treated with an isocyanate in the presence of base to form ureas ii of the present invention. The bases used act as acid scavenger and are typically tertiary amine bases such as triethylamine, diethylisopropylamine, N-methylmorpholine, pyridine and the like. Similarly, treatment of i with an appropriate isothiocyanate provides target thioureas iii. Conversion of iii to guanidines iv can be accomplished by treating iii with methyl iodide to form a corresponding S-methyl isothiourea, which can be treated with ammonium hydroxide to form the corresponding guanidine compound iv.

Alternatively, anilines such as 2-methoxy-5-pentafluorophenylsulfonamidoaniline can be treated with triphosgene and a suitable amine in the presence of an acid scavenger to provide ureas of the present invention (see Examples 7 and 8). A similar reaction with thiophosgene allows the synthesis of corresponding thioureas. These approaches are illustrated in Scheme 2.

SCHEME 2

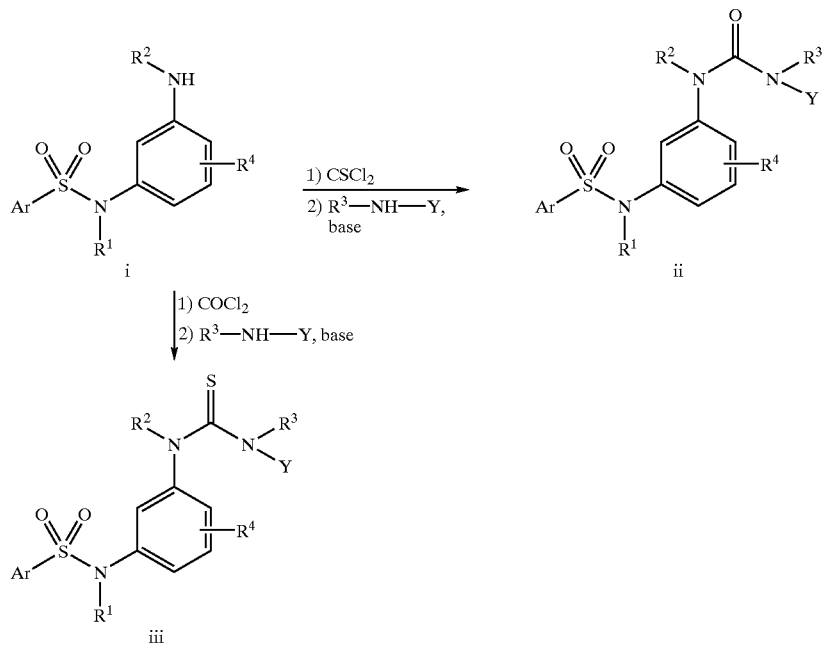

Still other methods of preparation are provided in Scheme 3. The methods presented in this scheme are typically employed when the Ar group is incompatible with the conditions for urea, thiourea and guanidine synthesis. Accordingly, treatment of a suitable nitroaniline derivative v with either an isocyanate or an isothiocyanate provides vi or viii, respectively. Reduction of the nitro group present in vi and viii can be accomplished using either hydrogenation with a palladium on charcoal catalyst (for vi) or tin chloride and HCl (for vi or viii). The anilines, thus produced (vii and ix) can each be sulfonylated with an appropriate aryl sulfonyl chloride ($ArSO_2Cl$) in the presence of an acid scavenging base. Additionally, ix can be converted to a guanidine derivative x using methyl iodide and ammonia (similar to the method described in Scheme 1). Conversion of x to the target compounds iv is accomplished by treating the aniline x with an aryl sulfonyl chloride.

SCHEME 3

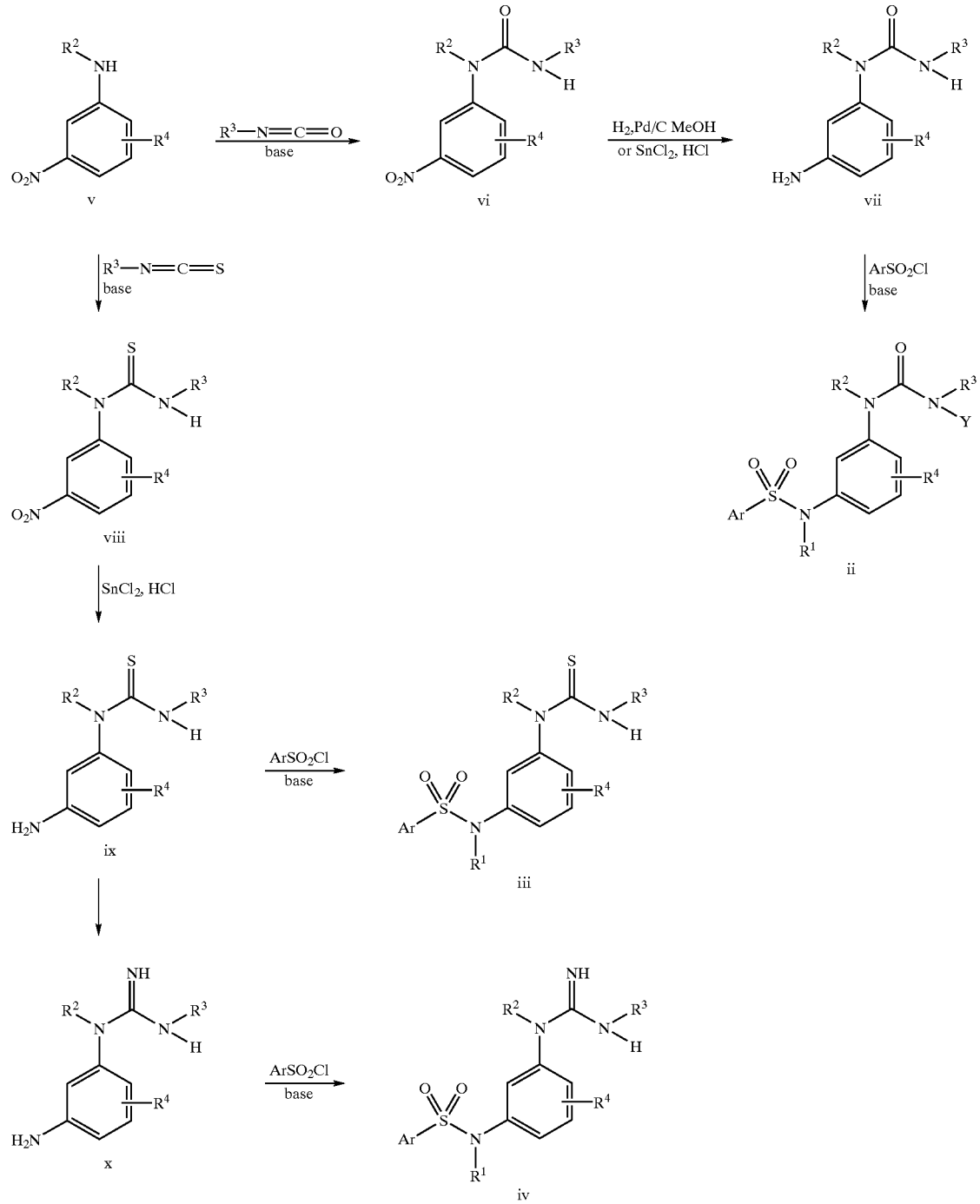

The compounds used as initial starting materials in this invention may be purchased from commercial sources or, alternatively, can be readily synthesized by standard procedures which are well known to those of ordinary skill in the art.

Some of the compounds of Formula I may exist as stereoisomers, and the invention includes all active stereoisomeric forms of these compounds. In the case of optically active isomers, such compounds may be obtained from corresponding optically active precursors using the procedures described above or by resolving racemic mixtures. The resolution may be carried out using various techniques such as chromatography, repeated recrystallization of derived asymmetric salts, or derivatization, which techniques are well known to those of ordinary skill in the art.

The compounds of the invention may be labeled in a variety of ways. For example, the compounds may contain radioactive isotopes such as, for example, $^3$H (tritium) and $^{14}$C (carbon-14). Similarly, the compounds may be advantageously joined, covalently or noncovalently, directly or through a linker molecule, to a wide variety of other compounds, which may provide pro-drugs or function as carriers, labels, adjuvents, coactivators, stabilizers, etc. Such labeled and joined compounds are contemplated within the present invention.

Analysis of Compounds

Representative compounds and compositions were demonstrated to have pharmacological activity in in vitro assays, e.g., they are capable of specifically modulating a cellular physiology to reduce an associated pathology or provide or enhance a prophylaxis.

Certain preferred compounds and compositions are capable of specifically regulating LDL receptor gene expression. Compounds may be evaluated in vitro for their ability to increase LDL receptor expression using western-blot analysis, for example, as described in Tam et al. (*J. Biol. Chem.* 1991, 266, 16764). Established animal models to evaluate hypocholesterolemic effects of compounds are known in the art. See, for example, Spady et al., *J. Clin. Invest.* 1988, 81, 300, Evans et al., *J. Lipid Res.* 1994, 35, 1634 and Lin et al., *J. Med. Chem.* 1995, 38, 277.

Certain preferred compounds and compositions display specific toxicity to various types of cells. Certain compounds and compositions of the present invention exert their cytotoxic effects by interacting with cellular tubulin. For certain preferred compounds and compositions of the present invention, that interaction is covalent and irreversible. Other compounds bind in a non-covalent manner. Compounds and compositions may be evaluated in vitro for their ability to inhibit cell growth, for example, as described in Ahmed et al., *J. Immunol. Methods* 1994, 170, 211. Established animal models to evaluate antiproliferative effects of compounds are also known in the art. For example, compounds can be evaluated for their ability to inhibit the growth of human tumors grafted into immunodeficient mice using methodology similar to that described by Rygaard and Povlsen, *Acta Pathol. Microbiol. Scand.* 1969, 77, 758, and Giovanella and Fogh, *Adv. Cancer Res.* 1985, 44, 69.

Formulation and Administration of Compounds and Pharmaceutical Compositions

The present invention provides methods of using the subject compounds and compositions to treat disease or provide medicinal prophylaxis, to slow down and/or reduce the growth of tumors, to upregulate LDL receptor gene expression in a cell, or to reduce blood cholesterol concentration in a host, etc. These methods generally involve contacting the cell with or administering to the host an effective amount of the subject compounds or pharmaceutically acceptable compositions.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally or intravenously in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically converted to the subject compound by the recipient host. A wide variety of pro-drug formulations are known in the art.

The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

The compositions may be advantageously combined and/or used in combination with other hypocholesterolemic or antiproliferative therapeutic or prophylactic agents, different from the subject compounds. In many instances, administration in conjunction with the subject compositions enhances the efficacy of such agents. Exemplary antiproliferative agents include cyclophosphamide, methotrexate, adriamycin, cisplatin, daunomycin, vincristine, vinblastine, vinarelbine, paclitaxel, docetaxel, tamoxifen, flutamide, hydroxyurea, and mixtures thereof. Exemplary hypocholesterolemic and/or hypolipemic agents include: bile acid sequestrants such as quaternary amines (e.g. cholestyramine and colestipol); nicotinic acid and its derivatives; HMG-CoA reductase inhibitors such as mevastatin, pravastatin, and simvastatin; gemfibrozil and other fibric acids, such as clofibrate, fenofibrate, benzafibrate and cipofibrate; probucol; raloxifene and its derivatives; and mixtures thereof.

The compounds and compositions also find use in a variety of in vitro and in vivo assays, including diagnostic assays. For example, various allotypic LDL receptor gene expression processes may be distinguished in sensitivity assays with the subject compounds and compositions, or panels thereof. In certain assays and in in vivo distribution studies, it is desirable to used labeled versions of the subject compounds and compositions, e.g. radioligand displacement assays. Accordingly, the invention provides the subject compounds and compositions comprising a detectable label, which may be spectroscopic (e.g. fluorescent), radioactive, etc.

The following examples are offered by way of illustration and not by way of limitation.

EXAMPLES $^1$H-NMR spectra were recorded on a Varian Gemini 400 MHz NMR spectrometer. Significant peaks are tabulated in the order: multiplicity (s, singlet; d, doublet; t, triplet; q, quartet; m, multiplet; br s, broad singlet), coupling constant (s) in Hertz and number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses).

Examples 1–4 provide the synthesis of certain useful intermediates. The remaining examples provide the preparation of pentafluorophenylsulfonamidobenzene ureas. One of skill in the art will appreciate that similar reaction schemes can be used to prepare the corresponding 2,3,4,5-tetrafluorophenylsulfonamidobenzene, 3,4,5-trimethoxyphenylsulfonamidobenzene, and 3-methoxy-4,5-methylenedioxyphenylsulfonamidobenzene derivatives. Preparation of the starting anilines for each of those series can be produced by reduction of the corresponding nitro-containing sulfonanilide compounds, similar to the process described in Example 3. These nitro compounds are obtained by reaction of the appropriate arylsulfonyl chlorides (described in co-pending applications Ser. Nos. 08/917,025 and 08/896,827) with the appropriate nitroanilines (known in the chemical literature).

Example 1

This example illustrates the preparation of intermediate 4-methoxy-3-nitroaniline.

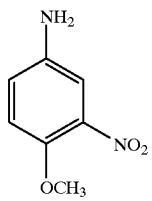

1

4-Methoxy-3-nitroaniline

To a 1M solution of 3-nitro-4-fluoroaniline (16.7 g, 107 mmol, from Aldrich Chemical Co., Milwaukee, Wis., USA) in anhydrous methanol at ambient temperature was added sodium methoxide (23.1 g, 428 mmol) and the resulting solution was refluxed with stirring for 21 hours. The reaction mixture was then cooled to 0° C. and a 12M solution of HCl (13.4 mL) was added dropwise followed by water (250 mL). The crude mixture was extracted three times with Et$_2$O (200 mL). The organic layers were combined, washed with brine (300 mL), dried over Na$_2$SO$_4$, and concentrated under vacuum to yield 17.5 g (97%) of product as a dark brown solid, which was used without further purification. $^1$H NMR (400MHz, DMSO-d$_6$) δ7.09 (d, J=9Hz, 1H), 7.01 (dd, J=2.8, 1.3Hz, 1H), 6.85 (ddd, J=9, 2.8, 1.4Hz, 1H), 5.2 (s, 2H), 3.75 (s, 3H).

Example 2

This example illustrates the synthesis of intermediate 2-nitro-4-pentafluoro-phenylsulfonamidoanisole.

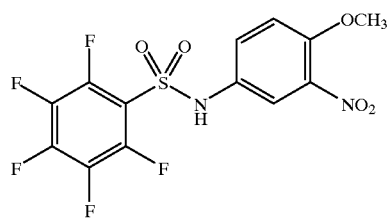

2

2-Nitro-4-pentafluorophenylsulfonamidoanisole

To a 0.4 M solution of 4-methoxy-3-nitroaniline (17.5 g, 104 mmol, prepared in Example 1), in anhydrous methanol was added dropwise pentafluorophenylsulfonyl chloride (7.7 mL, 52 mmol, from Aldrich Chemical Co.) and the resulting mixture was stirred at ambient temperature for 1 hour. The reaction mixture was concentrated under vacuum and purified by column chromatography (10–30% EtOAc in hexane) to yield 18.1 g (87%) of the title compound as an orange solid, mp 95–97° C. $^1$H NMR (400MHz, CDCl$_3$) δ7.64 (d, J=2.7Hz, 1H), 7.51 (dd, J=9, 2.7Hz, 1H), 7.09 (d, J=9.0Hz, 1H), 3.95 (s, 3H). MS (EI): m/z 817 (30, 2M+Na−2H), 398 (30, M+), 397 (100, M−H).

Example 3

This example illustrates the preparation of intermediate 2-methoxy-5-pentafluorophenylsulfonamidoaniline.

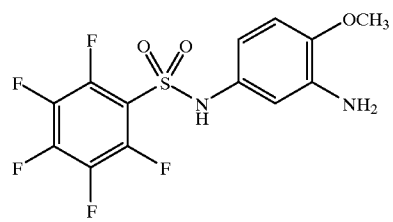

3

2-methoxy-5-pentafluorophenylsulfonamidoaniline

To a 0.15M solution of 2-nitro-4-pentafluorophenylsulfonamidoanisole (18.1 g, 45.5 mmol, prepared in Example 2), in 100% anhydrous ethanol was added 10% Pd/C (4.84 g, 4.55 mmol). Hydrogen gas was bubbled through the solution for 1 min and the resulting mixture was stirred for 24 h under 1 atmosphere of hydrogen. The crude reaction mixture was filtered through a pad of Celite and the filter pad was washed with ethanol (500 mL). The filtrate and wash were combined and concentrated under vacuum to yield 16.5 g (99%) of product as an off white solid which was used without further purification, mp 142–143° C. $^1$H NMR (400MHz, DMSO-d$_6$) δ10.64 (s, 1H), 6.68 (d, J=8.4 Hz, 1H), 6.44 (d, J=2.1 Hz, 1H), 6.3 (dd, J=8.4, 2.1 Hz, 1H), 4.88 (bs, 2H), 3.69 (s, 3H). MS(EI): m/z 369 (100, M+H).

Example 4

This example illustrate the preparation of intermediate 3-methylamino-4-methoxy-1-pentafluorophenylsulfonamidobenzene.

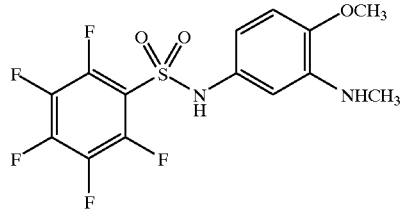

4

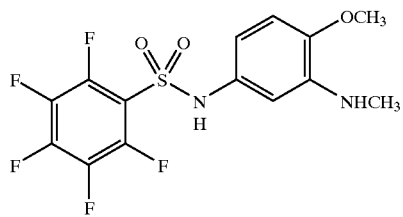

4

3-Methylamino-4-methoxy-1-pentafluorophenylsulfonamidobenzene

To a 0.5M solution of 2-formamido-4-nitroanisole (745 mg, 3.8 mmol) in dioxane was added sodium borohydride (722 mg, 19 mmol) followed by dropwise addition of glacial acetic acid (1.09 mL, 19 mmol). The reaction mixture was refluxed for 40 minutes, then cooled to 0° C. and quenched slowly with MeOH. Excess MeOH was then added and the solution was concentrated under vacuum to yield 2-methylamino-4-nitroanisole. The crude product was dissolved in anhydrous MeOH (20 mL) and Pd/C (795 mg, 0.76 mmol) was added followed by bubbling hydrogen gas through the solution for 1 minute. The reaction mixture was then stirred for 1.5 h under 1 atmosphere of hydrogen. The reaction mixture was filtered through a pad of Celite and the filter pad was washed with MeOH (40 mL). To the combined filtrate and wash was added pentafluorophenylsulfonyl chloride (282 mL, 0.26 mmol). After stirring for 30 min the reaction mixture was concentrated under vacuum and purified by column chromatography (10–25% EtOAc in hexane) to yield 153 mg (21% for three steps) of the title compound as a pale yellow solid. $^1$H NMR (400MHz, DMSO-$d_6$) δ10.7 (s, 1H), 6.68 (d, J=8.4 Hz, 1H), 6.3 (dd, J=8.3, 2.5 Hz, 1H), 6.22 (d, J=2.2 Hz, 1H), 5.18 (bs, 1H), 3.7 (s, 3H), 2.6 (d, J=3 Hz, 3H). MS(EI): m/z 785 (35, 2M+Na–2H), 382 (20, M+), 381 (100, M–H).

Example 5

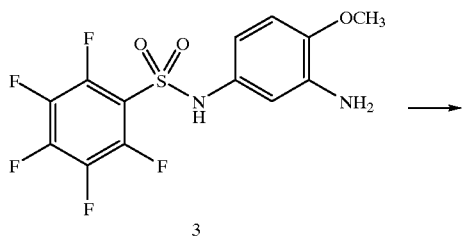

3

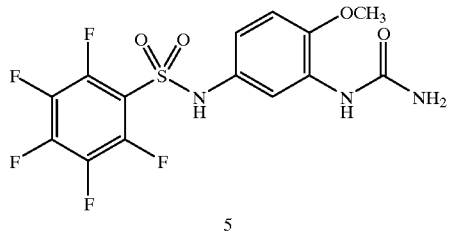

5

Potassium cyanate (36 mg, 0.45 mmol) dissolved in deionized water (0.75 mL) was added to 3 (150 mg, 0.41 mmol) dissolved in glacial acetic acid (3 mL). The cloudy reaction mixture was stirred at room temperature for 3 hours. The reaction mixture was poured into deionized water (50 mL) and extracted 3 times with ethyl acetate (25 mL). The combined organic layers were washed with saturated $NaHCO_3$ and saturated brine. The solution was dried over $MgSO_4$, filtered, and concentrated under reduced pressure. The resultant white solid was recrystallized from hot ethyl acetate/hexanes to give 5 (75 mg, 45%) as a white crystalline solid. mp 226° C. $^1$H NMR ($CD_3CN$): δ8.73 (bs, 1H); 7.95 (d, J=2.4 Hz, 1H); 7.39 (bs, 1H); 6.92–6.91 (m, 3H); 5.14 (bs, 2H); 3.83 (s, 3H). MS(ESI): m/z 410.0 (M–H).

The potassium salt of 5 was prepared by suspending 5 in deionized water and adding 1.0 equivalent of 1N KOH(aq). The mixture was shaken until solution was complete, then lyophilized to dryness. mp >250° C. $^1$H NMR ($D_2O$): δ7.12 (d, J=2.7 Hz, 1H); 6.96 (d, J=8.8 Hz, 1H); 6.76 (dd, J=2.7, 8.8 Hz, 1H); 3.83 (s, 3H).

Example 6

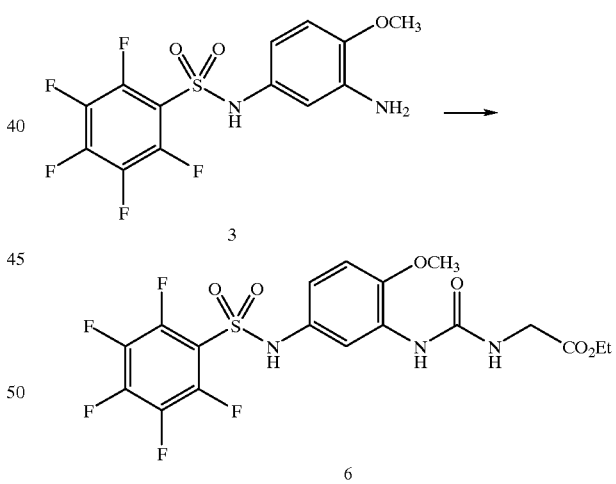

Ethyl isocyanatoacetate (17 mL, 0.15 mmol) was added to 3 (50 mg, 0.13 mmol) dissolved in chloroform (1.5 mL). The cloudy reaction mixture was stirred at room temperature for 1 hour, at which point the reaction mixture had solidified. Acetone (2 mL) and ethyl isocyanatoacetate (50 mL, 0.45 mmol) were added and the now homogeneous reaction mixture was heated to 50° C. After 1.5 hours, solvents were removed under reduced pressure and the resultant residue directly purified by flash chromatography (silica gel, 40% to 60% ethyl acetate/hexanes). Fractions containing the desired product were concentrated and the residue recrystallized from hot ethyl acetate/hexanes to give 6 (45 mg, 67%) as a white crystalline solid. mp 164–170° C. $^1$H NMR (CD$_3$CN): δ8.28 (bs, 1H); 7.92 (d, J=2.6 Hz, 1H); 7.45 (bs, 1H); 6.92 (d, J=8.7 Hz, 1H); 6.80 (dd, J=8.6, 2.6 Hz, 1H); 5.85 (bt, J=5.2 Hz, 1H); 4.15 (q, J=7.1 Hz, 2H); 3.86 (d, J=5.8 Hz, 2H); 3.84 (s, 3H); 1.24 (t, J=7.1 Hz, 3H). MS(ESI): m/z 496.0 (M–H).

Example 7

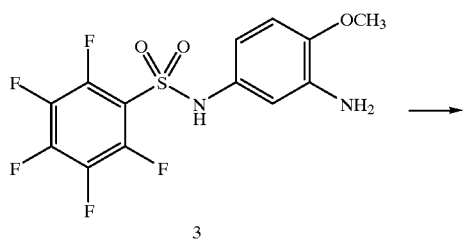

3

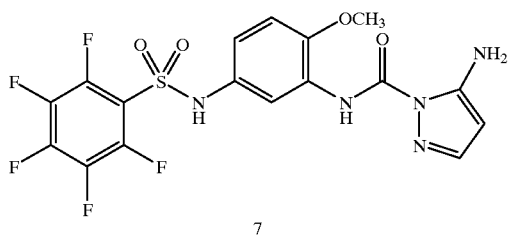

7

To a 25 mL round-bottom flask was added 204 mg (0.55 mmol) of 3 and 2.0 mL of dry THF. The mixture was stirred until the solid dissolved and then the flask was cooled to 0 ÿC in an ice-water bath. Solid triphosgene (54 mg, 0.18 mmol) was added to the mixture over a period of two minutes and the mixture was allowed to stir for an additional five minutes. Then 154 μL (112 mg, 1.11 mmol) of triethylamine was added dropwise (the mixture turned a cloudy, white color). The reaction mixture was then warmed to room temperature and stirred for 15 minutes. After cooling back down to 0ÿC, a solution of 46 mg (0.55 mmol) of 3-aminopyrazole in 2.0 mL of dry THF was added dropwise. The reaction mixture was once again heated to room temperature and was stirred for three hours.

The crude mixture was poured into 5 mL of 1N HCl and was extracted with three 20 mL volumes of ethyl acetate. The combined organics were washed with brine, dried over MgSO$_4$ and concentrated in vacuo to give an off-white solid. This was purified by silica gel flash chromatography (1:3 ethyl acetate:hexanes). The resulting white solid was recrystallized from ethyl acetate and hexanes to yield 172 mg (65%) of white crystals. mp 140–144° C. MS(ESI): m/z 476.0 (M–H). $^1$H NMR (DMSO-d$_6$): δ3.84 (s, 3H); 5.36 (d, J=1.2 Hz, 1H); 6.51 (s, 2H); 6.90 (dd, J$_1$=6.6 Hz, J$_2$=1.7 Hz, 1 H); 7.05 (d, J=6.6 Hz, 1H); 7.41 (s, 1H); 7.92 (d, J=1.7 Hz); 9.53 (s, 1H); 11.01 (s, 1 H). ES MS (M–H)$^-$ theory 476.0; observed 476.0. Anal. calcd. for C$_{17}$H$_{12}$F$_5$N$_5$O$_4$S: C 42.77, H 2.53, N 14.67. Found: C 43.05, H 2.48, N 14.47.

Example 8

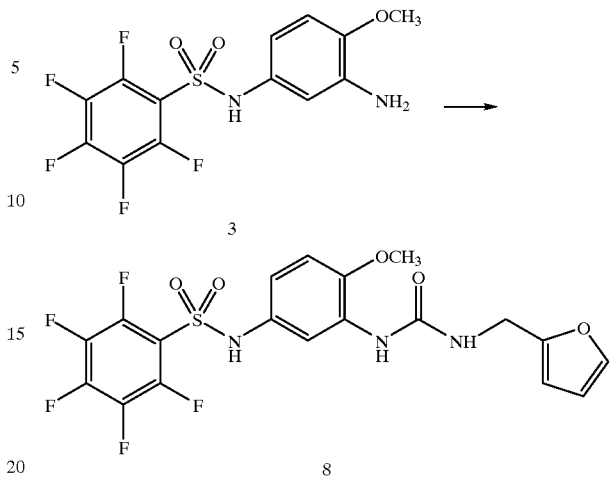

To a 25 mL round-bottom flask was added 206 mg (0.56 mmol) of 3 and 2.0 mL of dry THF. The mixture was stirred until the solid dissolved and then the flask was cooled to 0° C. in an ice-water bath. Solid triphosgene (55 mg, 0.19 mmol) was added to the mixture over a period of two minutes and the mixture was allowed to stir for an additional five minutes. Then 78 μL (57 mg, 1.12 mmol) of triethylamine was added dropwise (the mixture turned a cloudy, white color). The reaction mixture was then warmed to room temperature and stirred for 15 minutes. After cooling back down to 0° C., a solution of 55 mg (0.56 mmol) of 2-furfurylamine in 2.0 mL of dry THF was added dropwise. The reaction mixture was once again heated to room temperature and was stirred for two hours.

The crude mixture was poured into 5 mL of 1N HCl and was extracted with three 20 mL volumes of ethyl acetate. The combined organics were washed with brine, dried over MgSO$_4$ and concentrated in vacuo to give a clear oil. This oil was purified by silica gel flash chromatography (1:1 ethyl acetate:hexanes). The resulting white solid was triturated in methanol and collected by filtration to yield 234 mg (85%) of 8 as a white powder. mp 208° C. $^1$H NMR (DMSO-d$_6$): δ3.77 (s, 3H); 4.23 (d, J=4.2 Hz, 2H); 6.23 (d, J=2.3 Hz, 1H); 6.38 (dd, J$_1$=2.3 Hz, J$_2$=1.4 Hz, 1H); 6.68 (dd, J$_1$=5.4 Hz, J$_2$=2.0 Hz, 1H); 6.88 (d, J=6.6 Hz, 1H); 7.24 (m, 1H); 7.57 (t, J=0.6 Hz, 1H); 7.87 (d, J=1.9 Hz, 1H); 8.00 (s, 1H); 10.75 (s, 1 H). MS(ESI): 490.0 (M–H). Anal. Calcd. for C$_{19}$H$_{14}$F$_5$N$_3$O$_5$S: C 46.44, H 2.87, N 8.55. Found: C 46.64, H 2.89, N 8.52.

Example 9

This example illustrates an alternative synthesis of compound 5.

9.1 Formylation of 2-methoxy-5-nitroaniline

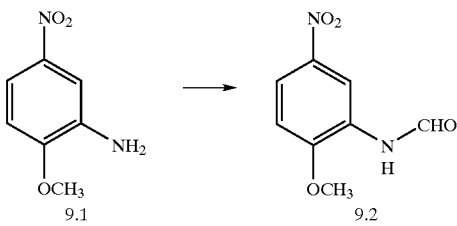

Formic acid (45 mL of 98%, 1.2 mol) was added dropwise to acetic anhydride (100 mL, 1.05 mol) at 0° C. over 15 minutes. The mixture was heated to 45–50° C. for 30 minutes, then cooled to 0° C. Anhydrous THF (100 mL) was then added to the reaction mixture. 2-Methoxy-5-nitroaniline (63 g, 375 mmol, TCI America) dissolved in anhydrous THF (200 mL) was added by addition funnel over 30 minutes. The orange/red color of the starting material instantly disappeared upon addition to the reaction mixture and a pale yellow solid slowly precipitated during the course of the addition. The addition funnel was rinsed with 50 mL of anhydrous THF. After the addition was complete, the reaction mixture was allowed to warm to room temperature over 30 minutes. The pale yellow precipitate was collected by filtration. The filtrate was then concentrated, triturated with ether, and the solid again collected by filtration. After drying under high vacuum, 70.4 g (96%) of formamide 9.2 was obtained.

$^1$H NMR (CD$_3$COCD$_3$): δ9.34 (bs, 1H); 8.55 (s, 1H); 8.03 (dd, J=2.8, 9.1 Hz, 1H); 7.26 (d, J=9.1 Hz, 1H); 4.07 (s, 3H). MS (ESI): m/z 197.1 (MH$^+$), 219.1 (MNa$^+$), 337 (2[MNa$^+$]—H).

9.2 Reduction of 9.2

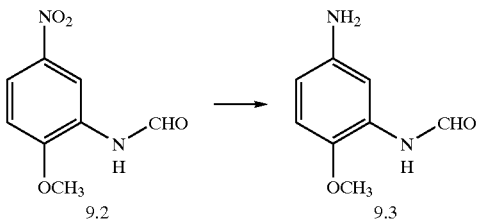

A 500 mL 3-neck flask was charged with 10 g of formamide 9.2 and 1 g of 3% Pd on carbon catalyst. The mixture was suspended in 100 mL of MeOH, and placed under an atmosphere of hydrogen (balloon pressure). After stirring vigorously for 4 h, TLC demonstrated consumption of the starting material. The reaction mixture was filtered and the residue washed 3 times with 100 mL of hot acetone to ensure complete dissolution of the product. The filtrate was concentrated, triturated with acetone, and the product collected by filtration. After drying under high vacuum, 7.51 g (88%) of aniline 9.3 was obtained.

$^1$H NMR (CD$_3$COCD$_3$): δ8.72 (bs, 1H); 8.39 (s, 1H); 7.78 (s, 1H); 6.73 (d, J=8 Hz, 1H); 7.26 (dd, J=2, 8 Hz, 1H); 4.28 (bs, 2H); 3.73 (s, 3H). MS (ESI): m/z 167.1 (MH$^+$), 189.1 (MNa$^+$).

9.3 Sulfonylation of 9.3

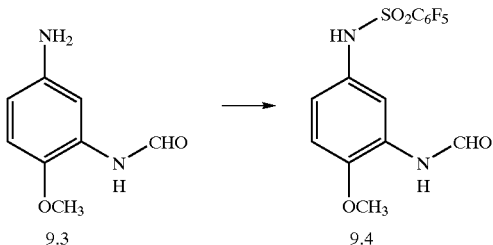

Aniline 9.3 (44.6 g, 268 mmol) and 2,6-lutidine (32.8 mL, 282 mmol) were dissolved in 800 mL of acetone (the aniline only partly dissolved). An addition funnel was charged with C$_6$F$_5$SO$_2$Cl (41.8 mL, 282 mmol) and the sulfonyl chloride was added over 15 minutes. During the addition, the starting material dissolved and a new precipitate (2,6-lutidine hydrochloride) formed. After 30 minutes, the 2,6-lutidine hydrochloride was removed by filtration and the filtrate concentrated under reduced pressure. The brown oily solid so produced was triturated with CH$_2$Cl$_2$ and the solid collected. A second batch of product was obtained by repeating the concentration, trituration, and filtration. After drying under high vacuum, 95.5 g (90%) of sulfonamide 9.4 was obtained as a pale yellow solid.

$^1$H NMR (CD$_3$COCD$_3$): δ9.55 (bs, 1H); 9.01 (bs, 1H); 8.39 (s, 1H); 8.17 (d, J=2.6 Hz, 1H); 7.06 (dd, J=2.6, 8.8 Hz, 1H); 6.99 (d, J=8.8 Hz, 1H); 3.86 (s, 3H). MS (ESI): m/z 395.0 (M-H), 812.9 (2[M-H]+Na).

9.4 Removal of formyl group from 9.4

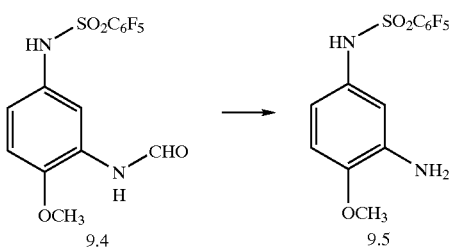

Acetyl chloride (18.8 mL, 265 mmol) was carefully added to absolute ethanol (360 mL). The mixture grew very warm (~60° C.). After allowing the solution of ethanolic HCl to cool to room temperature, a suspension of sulfonamide 9.4 (95.4 g, 241 mmol) in 360 mL of absolute ethanol was added. An additional 280 mL of absolute ethanol was used to rinse all the starting material into the reaction mixture. All solids dissolved within 2.5 hours. After 20 h, the reaction mixture was concentrated under reduced pressure to ~100 mL total volume. The white precipitate was collected by filtration, then rinsed sequentially with ethanol and hexanes. The filtrate was again concentrated and the precipitate collected and rinsed. After drying under high vacuum, 103.6 g (95%) of sulfonamide 9.5 (as the hydrochloride salt with one ethanol of solvation) was obtained as fine white crystals.

$^1$H NMR (CD$_3$OD): δ7.40 (d, J=2.4 Hz, 1H); 7.15–7.21 (m, 2H); 4.85 (bs, 5H); 3.94 (s, 3H); 3.60 (q, J=7.0 Hz, 2H); 1.18 (t, J=7.0 Hz, 3H). MS (ESI): m/z 369.0 (MH$^+$).

9.5 Conversion of 9.5 to 5

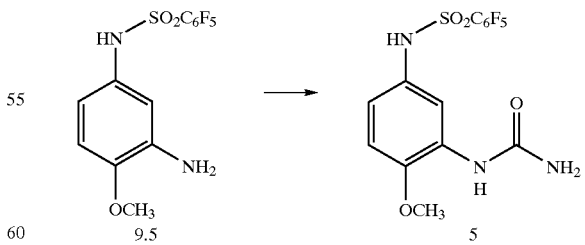

Potassium cyanate (1.72 g, 21 mmol) dissolved in deionized water (7 mL) was added to sulfonamide 9.5 (7.13 g, 19.4 mmol) dissolved in glacial acetic acid (70 mL) and water (10 mL) at 0° C. The cloudy reaction mixture was stirred for 2 hours. The reaction mixture was poured into deionized water (300 mL) and the white precipitate was collected by filtration. After drying under a stream of air, the product was dissolved in hot EtOAc (400 mL) and the solution was heated to reflux. Ethyl acetate was distilled out of the flask until a very slight cloudiness was noted in the solution. The solution was allowed to cool to room temperature then placed in a refrigerator for 16 h. White crystals were collected by filtration, rinsed with hexanes, and dried under high vacuum to yield 7.33 g of 5. (NMR analysis shows that these crystals are ~20% by weight ethyl acetate even after drying under high vacuum. Additional amounts of 5 can be recovered by concentrating the mother liquor and repeating the crystallization process).

$^1$H NMR(CD$_3$OD): δ7.82 (s, 1H); 6.88 (s, 2H); 7.39 (bs, 1H); 3.85 (s, 3H). MS (ESI): m/z 410.0 (M−H).

9.6 Preparation of the sodium salt of 5

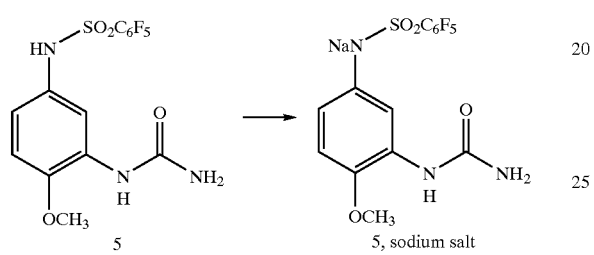

Compound 5 (1.0 g, 2.41 mmol) was suspended in deionized water (10 mL). Sodium hydroxide solution (2.51 M, 1.0 mL, 2.5 mmol) was added dropwise with vigorous stirring. Additional NaOH solution was added dropwise until the pH of the medium was ~10.5 and all solids had dissolved. The aqueous solution of compound 5 sodium salt was filtered to remove a very small amount of insoluble material. The solution was then saturated with NaCl. After 10 minutes, the precipitate of compound 5, sodium salt was collected and washed with saturated brine. The collected solid was dried under a stream of air for 5 minutes, then acetone was added to dissolve the sodium salt of compound 5. The solution was filtered (leaving behind excess NaCl) and the residue was washed with acetone. The acetone solution was filtered a second time, then concentrated under reduced pressure. The residue was dissolved in hot acetone, and sufficient hexanes added until a very slight cloudiness was seen. On cooling, the title compound crystallized. The precipitate was collected, rinsed with hexanes, and dried under high vacuum to give 0.73 g (70%) of compound 5, sodium salt as white crystals.

$^1$H NMR (D$_2$O): δ7.14 (d, J=2.6 Hz, 1H); 6.93 (d, J=8.8 Hz, 1H); 6.74 (dd, J=2.5, 8.7 Hz, 1H); 3.80 (s, 3H). MS (ESI): m/z 410.0 (M−H)

Example 10

Assessment of Biological Activity

The ability of test compounds to arrest the growth of tumor cells in culture was evaluated using HeLa cells, derived from a human cervical adenocarcinoma, and obtained from the American Type Culture Collection (ATCC, Rockville, Md.). Cells were grown in culture in the usual way. Test compounds were dosed in triplicate at concentrations ranging from 5 nM to 50 μM, and the cellular growth rate was calculated by harvesting the cells after 72 hours of treatment and measuring their metabolic activity using an Alamar Blue assay (Biosource International, Camarillo, Calif.). The degree of metabolic activity in the culture is proportional to the number of living cells. See, Ahmed et al., J. Immunol. Methods 1994, 170, 211. The change in growth rate for cells treated with test compounds was normalized to the growth of untreated cells and a plot of normalized cellular growth vs. compound concentration was made. The concentration at which total growth inhibition (TGI) occurred was determined. Compounds were similarly evaluated for cell growth inhibition using MCF-7/ADR cells.

TABLE 1

Arylsulfonanilide Ureas

| Compound | R | HeLa TGI | MCF-7/ADR TGI |
|---|---|---|---|
| 5 | —NH$_2$ | +++ | +++ |
| 6 | —NH—CH$_2$—CO$_2$Et | + | + |
| 7 | pyrazole-NH$_2$ | +++ | +++ |
| 8 | —NH—CH$_2$-furan | +++ | +++ |
| 9 | morpholine | ++ | ++ |
| 10 | —NH—CH$_2$—CH(OH)—CH$_2$OH | ++ | ++ |
| 11 | —NH—CH$_2$—CONH$_2$ | + | + |

TABLE 1-continued

Arylsulfonanilide Ureas

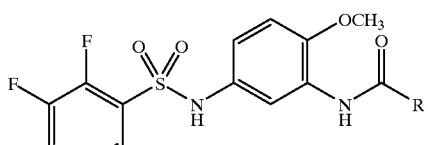

| Compound | R | HeLa TGI | MCF-7/ADR TGI |
|---|---|---|---|
| 12 | -CH(CH2OH)2) | + | + |
| 13 | | ++ | + |
| 14 | | ++ | + |
| 15 | 2) | + | + |
| 16 | | ++ | + |
| 17 | | + | + |
| 18 | | +++ | +++ |
| 19 | | +++ | ++ |
| 20 | | ++ | ++ |

TABLE 1-continued

Arylsulfonanilide Ureas

| Compound | R | HeLa TGI | MCF-7/ADR TGI |
|---|---|---|---|
| 21 | | ++ | + |

+++: TGI < 5;
++: TGI 5 to 40;
+: TGI > 40 ($\mu$M)

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

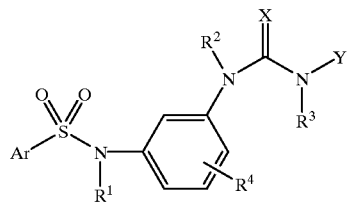

or a pharmaceutically acceptable salt thereof, wherein

X is a member selected from the group consisting of O, S and NH;

$R^1$ and $R^2$ are each members independently selected from the group consisting of hydrogen, $(C_1-C_6)$alkyl and $(C_1-C_6)$heteroalkyl;

$R^3$ is a member selected from the group consisting of hydrogen, $(C_1-C_6)$alkyl and $(C_1-C_6)$heteroalkyl, or is combined with Y and the nitrogen atom to which each is attached to form a 5-, 6- or 7-membered heterocyclic ring;

$R^4$ is a member selected from the group consisting of hydrogen, halogen, $(C_1-C_8)$alkyl, $(C_1-C_8)$heteroalkyl, $-OR^{11}$, $-SR^{11}$ and $-NR^{11}R^{12}$, wherein $R^{11}$ and $R^{12}$ are each independently selected from the group consisting of hydrogen, $(C_1-C_8)$alkyl and $(C_1-C_8)$heteroalkyl;

Y is a member selected from the group consisting of a heterocyclic ring, heterocyclyl$(C_1-C_4)$alkyl and heterocyclyl($C_1$–$C_4$)heteroalkyl, or is optionally linked together with $R^3$ to form a 5-, 6- or 7-membered heterocyclic ring; and Ar is a member selected from the group consisting of:

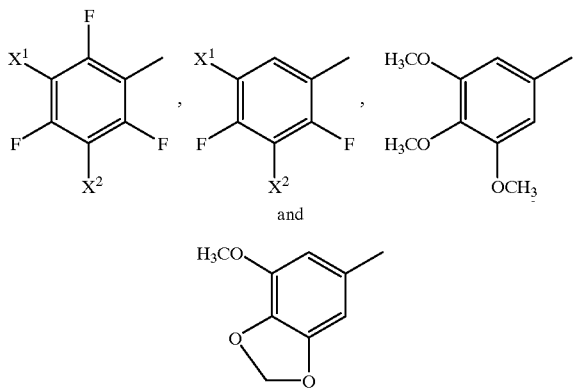

and wherein
$X^1$ and $X^2$ are each independently selected from the group consisting of F, Cl and Br.

2. A compound of claim 1, wherein X is O.

3. A compound of claim 1, wherein X is S.

4. A compound of claim 1, wherein X is NH.

5. A compound of claim 1, wherein Y is a heterocyclic ring.

6. A compound of claim 1, wherein Y is combined with $R^3$ and the nitrogen atom to which each is attached to form a 5- or 6-membered heterocycle.

7. A compound of claim 1, wherein Y is selected from the group consisting of 2-thiazolyl, 1,2,4-triazolyl, 1,3,4-thiadiazolyl, pyrazolyl, 1,2,3,4-tetrazolyl, imidazolyl, oxazolyl and 1,2,3-triazolyl.

8. A compound of claim 1, wherein $R^4$ is selected from the group consisting of hydrogen, ($C_1$–$C_3$)alkyl and ($C_1$–$C_3$) alkoxy.

9. A compound of claim 1, wherein $R^1$, $R^2$ and $R^3$ are each hydrogen and $R^4$ is ($C_1$–$C_3$)alkoxy.

10. A compound of claim 1, wherein $R^1$ and $R^2$ are each hydrogen and Y is combined with $R^3$ and the nitrogen atom to which each is attached to form a 5- or 6-membered heterocycle.

11. A compound of claim 1, wherein Ar is pentafluorophenyl.

12. A compound of claim 1, wherein Ar is 2,3,4,5-tetrafluorophenyl.

13. A compound of claim 1, wherein Ar is 3,4,5-trimethoxyphenyl.

14. A compound of claim 1, wherein Ar is 3-methoxy-4,5-methylenedioxyphenyl.

15. A compound of claim 1, represented by the formula:

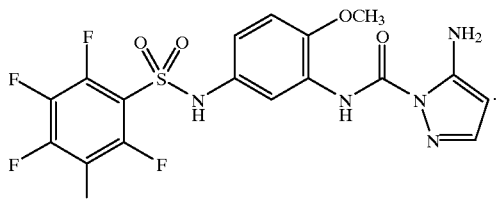

16. A compound of claim 1, represented by the formula:

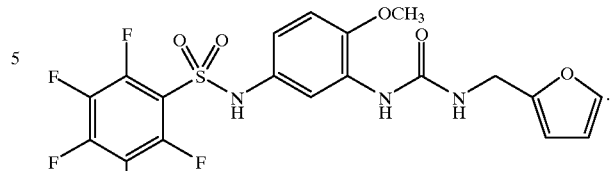

17. A compound of claim 1, represented by the formula:

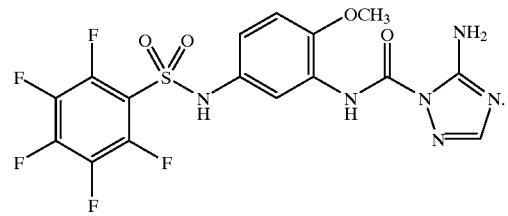

18. A pharmaceutical composition comprising a pharmaceutically acceptable excipient and a compound having the formula:

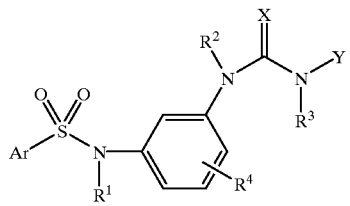

or a pharmaceutically acceptable salt thereof, wherein

X is a member selected from the group consisting of O, S and NH;

$R^1$ and $R^2$ are each members independently selected from the group consisting of hydrogen, ($C_1$–$C_6$)alkyl and ($C_1$–$C_6$)heteroalkyl;

$R^3$ is a member selected from the group consisting of hydrogen, ($C_1$–$C_6$)alkyl and ($C_1$–$C_6$)heteroalkyl, or is combined with Y and the nitrogen atom to which each is attached to form a 5-, 6- or 7-membered heterocyclic ring;

$R^4$ is a member selected from the group consisting of hydrogen, halogen, ($C_1$–$C_8$)alkyl, ($C_1$–$C_8$)heteroalkyl, —$OR^{11}$, —$SR^{11}$ and —$NR^{11}R^{12}$, wherein $R^{11}$ and $R^{12}$ are each independently selected from the group consisting of hydrogen, ($C_1$–$C_8$)alkyl and ($C_1$–$C_8$) heteroalkyl;

Y is a member selected from the group consisting of a heterocyclic ring, heterocyclyl($C_1$–$C_4$)alkyl and heterocyclyl($C_1$–$C_4$)heteroalkyl, or is optionally linked together with $R^3$ to form a 5-, 6- or 7-membered heterocyclic ring; and Ar is a member selected from the group consisting of:

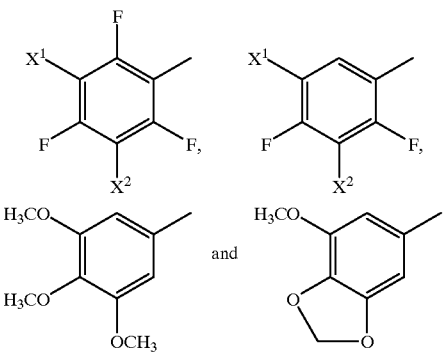

wherein
X¹ and X² are each independently selected from the group consisting of F, Cl and Br.

19. A composition of claim 18, wherein Ar is selected from the group consisting of

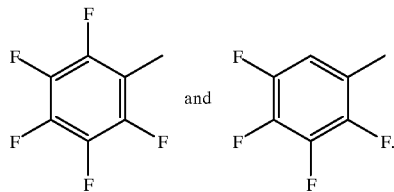

20. A composition of claim 18, wherein Ar is pentafluorophenyl.

21. A composition of claim 18, wherein Ar is 2,3,4,5-tetrafluorophenyl.

22. A composition of claim 18, wherein Ar is 3,4,5-trimethoxyphenyl.

23. A composition of claim 18, wherein Ar is 3-methoxy-4,5-methylenedioxyphenyl.

24. A composition of claim 18, further comprising an antiproliferative agent selected from the group consisting of cyclophosphamide, methotrexate, adriamycin, cisplatin, daunomycin, vincristine, vinblastine, vinarelbine, paclitaxel, docetaxel, tamoxifen, flutamide, hydroxyurea, and mixtures thereof.

25. A composition of claim 18, further comprising a member selected from the group consisting of hypocholesterolemic and hypolipemic agents.

26. A method of treating or preventing a disease state characterized by abnormally high levels of low density lipoprotein particles or cholesterol in the blood, or by an abnormally high level of cell proliferation, which method comprises administering to a mammalian subject in need thereof a therapeutically effective amount of a composition comprising a compound of formula:

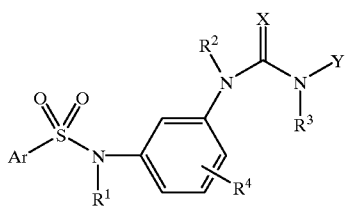

or a pharmaceutically acceptable salt thereof, wherein

X is a member selected from the group consisting of O, S and NH;

$R^1$ and $R^2$ are each members independently selected from the group consisting of hydrogen, $(C_1-C_6)$alkyl and $(C_1-C_6)$heteroalkyl;

$R^3$ is a member selected from the group consisting of hydrogen, $(C_1-C_6)$alkyl and $(C_1-C_6)$heteroalkyl, or is combined with Y and the nitrogen atom to which each is attached to form a 5-, 6- or 7-membered heterocyclic ring;

$R^4$ is a member selected from the group consisting of hydrogen, halogen, $(C_1-C_8)$alkyl, $(C_1-C_8)$heteroalkyl, $-OR^{11}$, $-SR^{11}$ and $-NR^{11}R^{12}$, wherein $R^{11}$ and $R^{12}$ are each independently selected from the group consisting of hydrogen, $(C_1-C_8)$alkyl and $(C_1-C_8)$heteroalkyl;

Y is a member selected from the group consisting of a heterocyclic ring, heterocyclyl$(C_1-C_4)$alkyl and heterocyclyl$(C_1-C_4)$heteroalkyl, or is optionally linked together with $R^3$ to form a 5-, 6- or 7-membered heterocyclic ring; and Ar is a member selected from the group consisting of:

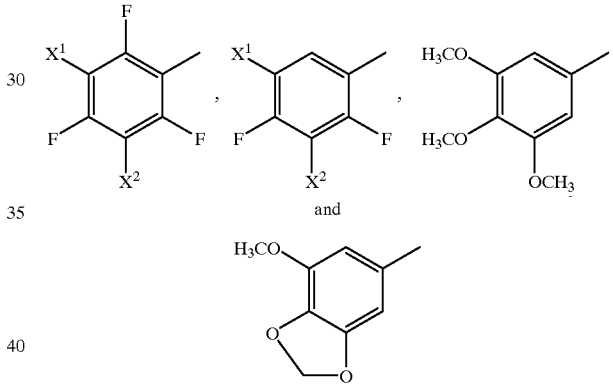

wherein
X¹ and X² are each independently selected from the group consisting of F, Cl and Br.

27. A method in accordance with claim 26, wherein the disease state is cancer or a cancerous condition.

28. A method in accordance with claim 26, wherein the proliferative disease state is infection by a microorganism.

29. A method in accordance with claim 26, wherein the proliferative disease state is psoriasis.

30. A method in accordance with claim 26, wherein the proliferative disease state is vascular restenosis.

31. A method in accordance with claim 26, wherein the disease state is hypercholesterolemia or another disease state associated with abnormally high levels of cholesterol or lipoproteins.

32. A method in accordance with claim 26, wherein the compound is administered orally.

33. A method in accordance with claim 26, wherein the compound is administered intravenously, intramuscularly, subcutaneously or intraduodenally.

* * * * *